(12) United States Patent
Zang (10) Patent No.: US 7,972,848 B2
(45) Date of Patent: Jul. 5, 2011

(54) ISOLATION AND IDENTIFICATION OF CROSS-REACTIVE T CELLS

(75) Inventor: Jingwu Z. Zang, Missouri City, TX (US)

(73) Assignee: Opexa Therapeutics, Inc., The Woodlands, TX (US)

(*) Notice: Subject to any disclaimer, the term of this patent is extended or adjusted under 35 U.S.C. 154(b) by 17 days.

(21) Appl. No.: 12/544,187

(22) Filed: Aug. 19, 2009

(65) Prior Publication Data

US 2009/0311229 A1 Dec. 17, 2009

Related U.S. Application Data

(63) Continuation of application No. 10/541,115, filed as application No. PCT/US03/41284 on Dec. 23, 2003, now abandoned.

(60) Provisional application No. 60/437,369, filed on Dec. 31, 2002.

(51) Int. Cl.
*C12N 5/071* (2010.01)
*A61K 38/04* (2006.01)
*C07K 5/00* (2006.01)
*C07K 7/00* (2006.01)
*C07K 16/00* (2006.01)
*C07K 17/00* (2006.01)

(52) U.S. Cl. ..................... 435/372.3; 530/327

(58) Field of Classification Search .................. None
See application file for complete search history.

(56) References Cited

U.S. PATENT DOCUMENTS

| 4,683,202 A | 7/1987 | Mullis |
| 5,614,192 A | 3/1997 | Vandenbark |
| 6,303,314 B1 | 10/2001 | Zhang |
| 7,658,926 B2 | 2/2010 | Zhang |

FOREIGN PATENT DOCUMENTS

WO  WO 99/13904  3/1999

OTHER PUBLICATIONS

Cirone et al., 2002, J. Med. Vir. vol. 68: 268-272.*
Zhang et al., 1996, J. Mol. Med. vol. 74: 653-662.*
Brosterhus et al., 1999, Eur. J. Immunol. vol. 29: 4053-4059.*
Tejada-Simon et al., 2001, Eur. J. Immunol. vol. 31: 907-917.*
Tejada-Simon et al., 2003, Ann Neurol. vol. 53: 189-197.*
Ben-Nun, et al., "Vaccination against autoimmune encephalomyelitis with T-lymphocite line cells reactive against myelin basic protein," Nature, 292:60-61 (1981).
Challoner, P.B., et al., "Plaque-associated expression of human herpesvirus 6 in multiple sclerosis," Proc. Natl. Acad. Sci., USA, 92:7440-44 (1995).
Cirone, M., et al., "Human Herpesvirus 6 and Multiple Sclerosis: A Study of T Cell Cross-Reactivity to Viral and Myelin Basic Protein Antigens," J. Med. Virol., 68:268-272 (2002).
Hong, et al., J. Immunol., 163:3530-3538 (1999).
Lider, et al., Science, 239:181-83 (1988).
Lohse, et al., Science, 244:820-822 (1989).
U.S. Appl. No. 60/386,287, filed May 6, 2002, Zhang, Jingwu Z.
U.S. Appl. No. 60/405,521, filed Aug. 23, 2002, Mattern, Rene.
Medaer, et al., "Depletion of myelin-basic-protein autoreactive T cells by T-cell vaccination: pilot trial in multiple sclerosis," Lancet, 346:807-808 (1995).
Stinissen, P., et al., "gammadelta T Cell Responses to Activated T Cells in Multiple Sclerosis Patients Induced by T Cell Vaccination," J. of Neuroimmunology, 87:94-104 (1998).
Stinissen, P., et al., "Vaccination with Autoreactive T Cell Clones in Multiple Sclerosis: Overview of Immunological and Clinical Data," J. of Neuroscience Research, 45(4):500-511 (1996).
Supplementary European Search Report of EP 03 80 0185 dated Jan. 9, 2006.
Tejada-Simon, M., et al., "Cross-Reactivity with Myelin Basic Protein and Human Herpesvirus-6 in Multiple Sclerosis," Annals of Neurology, 53(2):189-197 (2003).
Tejada-Simon, M., et al., "Detection of Viral DNA and Immune Responses to the Human Herpesvirus 6 101-Kilodalton Virion Protein in Patients with Multiple Sclerosis and in Controls," J. Virol., 76(12):6147-6154 (2002).
Vandevyer, et al., Eur. J. Immunol., 25:958-968 (1995).
Wucherpfennig, et al., J. Immunol., 152:5581-5592 (1994).
Zang, et al., "Restricted TCR V* gene rearrangements in T cells recongizing an immunodominant peptide of myelin basic protein in DR2 patients with multiple sclerosis," Intern Immunol. 10:991-998 (1998).
Zhang, et al., "T cell vaccination in multiple sclerosis: results of a preliminary study," J. Neurol., 249:212-8 (2002).
Zhang, J., et al., "MHC-Restricted Depletion of Human Myelin Basic Protein-Reactive T Cells by T Cell Vaccination," Science, 261:1451-1454 (1993).
Zhang, J., et al., "T Cell Vaccination: Clinical Application in Autoimmune Diseases," J. of Molecular Medicine, 74(11):653-662 (1996).

* cited by examiner

*Primary Examiner* — Amy E Juedes
(74) *Attorney, Agent, or Firm* — Todd Lorenz; Arnold & Porter LLP (57) ABSTRACT

Cross-reactive T cells recognizing both $MBP_{93-105}$ and $HHV-6_{1-13}$ peptides represent a significant subset of T cells with some degree of TCR degeneracy. It appears that the recognition of the cross-reactive T cells has a less stringent requirement for the flanking residues of the two peptides. In contrast, these flanking residues are critical for the T cell recognition of mono-specific T cells. The association between HHV-6 and autoreactive immune responses to MBP indicates that cross-reactive T cells, peptides from the V-D-J region of the T cell receptor from autoreactive T cells, and antiviral agents may prevent or treat MS.

10 Claims, 4 Drawing Sheets

SEQUENCE LISTING

<160> NUMBER OF SEQ ID NOS: 13

<210> SEQ ID NO 1
<211> LENGTH: 24
<212> TYPE: PRT
<213> ORGANISM: Homo sapiens

<400> SEQUENCE: 1

Tyr Leu Cys Ala Ser Ser Leu Val Arg Asp Ser Gly Tyr Thr Phe Gly
1               5                   10                  15

Ser Gly Thr Arg Leu Thr Val Val
            20

<210> SEQ ID NO 2
<211> LENGTH: 26
<212> TYPE: PRT
<213> ORGANISM: Homo sapiens

<400> SEQUENCE: 2

Tyr Phe Cys Ala Ser Ser Glu Asn Arg Ala Ser Tyr Asn Glu Gln Phe
1               5                   10                  15

Phe Gly Pro Gly Thr Arg Leu Thr Val Leu
            20                  25

<210> SEQ ID NO 3
<211> LENGTH: 26
<212> TYPE: PRT
<213> ORGANISM: Homo sapiens

<400> SEQUENCE: 3

Tyr Phe Cys Ala Ser Ser Leu Gly Arg Leu Ile Asn Ser Pro Leu His
1               5                   10                  15

Phe Gly Asn Gly Thr Arg Leu Thr Val Thr
            20                  25

<210> SEQ ID NO 4
<211> LENGTH: 24
<212> TYPE: PRT
<213> ORGANISM: Homo sapiens

<400> SEQUENCE: 4

Tyr Phe Cys Ala Ile Ser Glu Asp Gly Asn Tyr Gly Tyr Thr Phe Gly
1               5                   10                  15

Ser Gly Thr Arg Leu Thr Val Val
            20

<210> SEQ ID NO 5
<211> LENGTH: 27
<212> TYPE: PRT
<213> ORGANISM: Homo sapiens

<400> SEQUENCE: 5

Tyr Phe Cys Ala Ser Ser Leu Arg Ala Gly Gly Tyr Gln Tyr Gly Tyr
1               5                   10                  15

Thr Phe Gly Ser Gly Thr Arg Leu Thr Val Val
            20                  25

<210> SEQ ID NO 6
<211> LENGTH: 25
<212> TYPE: PRT
<213> ORGANISM: Homo sapiens

```
<400> SEQUENCE: 6

Phe Tyr Ile Cys Ser Ala Ser Leu Gly Met Gly Asp Ile Gln Tyr Phe
1               5                   10                  15

Gly Ala Gly Thr Arg Leu Ser Val Leu
            20                  25

<210> SEQ ID NO 7
<211> LENGTH: 15
<212> TYPE: PRT
<213> ORGANISM: Homo sapiens

<400> SEQUENCE: 7

Ala Ser Ser Glu Asn Arg Ala Ser Tyr Asn Glu Gln Phe Phe Gly
1               5                   10                  15

<210> SEQ ID NO 8
<211> LENGTH: 13
<212> TYPE: PRT
<213> ORGANISM: Homo sapiens

<400> SEQUENCE: 8

Ile Val Thr Pro Arg Thr Pro Pro Pro Ser Gln Gly Lys
1               5                   10

<210> SEQ ID NO 9
<211> LENGTH: 13
<212> TYPE: PRT
<213> ORGANISM: Homo sapiens

<400> SEQUENCE: 9

Met Asp Arg Pro Arg Thr Pro Pro Pro Ser Tyr Ser Glu
1               5                   10

<210> SEQ ID NO 10
<211> LENGTH: 8
<212> TYPE: PRT
<213> ORGANISM: Homo sapiens

<400> SEQUENCE: 10

Leu Gly Arg Ala Gly Leu Thr Tyr
1               5

<210> SEQ ID NO 11
<211> LENGTH: 4
<212> TYPE: PRT
<213> ORGANISM: Homo sapiens

<400> SEQUENCE: 11

Pro Arg Thr Pro
1

<210> SEQ ID NO 12
<211> LENGTH: 16
<212> TYPE: PRT
<213> ORGANISM: Homo sapiens

<400> SEQUENCE: 12

Asn Pro Val Val His Phe Phe Lys Asn Ile Val Thr Pro Arg Thr Pro
1               5                   10                  15

<210> SEQ ID NO 13
<211> LENGTH: 20
<212> TYPE: PRT
<213> ORGANISM: Homo sapiens
```

```
<400> SEQUENCE: 13

Ser Lys Ile Phe Lys Leu Gly Gly Arg Asp Ser Arg Ser Gly Ser Pro
1               5                   10                  15

Met Ala Arg Arg
            20
```

ISOLATION AND IDENTIFICATION OF CROSS-REACTIVE T CELLS

CROSS-REFERENCE TO RELATED APPLICATIONS

This is a continuation of U.S. patent application Ser. No. 10/541,115, filed on Apr. 12, 2006, which is the national stage of International Application No. PCT/US03/41284, filed on Dec. 23, 2003, which claims the benefit of U.S. Provisional Patent Application No. 60/437,369, filed on Dec. 31, 2002, the contents of all of which are incorporated herein by reference.

The Sequence Listing, which is part of the present disclosure, includes a 3 KB computer readable .txt file titled "5202US3 ST25.txt" generated by U.S. Patent & Trademark Office PatentIn version 3.5 software on Dec. 22, 2010 comprising nucleotide and/or amino acid sequences of the present invention. The subject matter of the Sequence Listing is incorporated herein by reference in its entirety.

FIELD OF THE INVENTION

The present invention relates generally to the field of diagnosis and treatment of autoimmune disease, such as multiple sclerosis (MS). More particularly, it concerns the isolation of cross-reactive T cells that are specific for self-antigens and foreign antigens. In addition, the present invention concerns the use of cross-reactive T cells for the diagnosis and treatment of autoimmune disease, such as MS.

BACKGROUND

Intercellular recognition complexes formed by T cell receptors (TCR) on cytotoxic T lymphocytes or T helper cells and MHC/peptide complexes on antigen presenting cells (APC) are a common recognition component in a diverse set of cell-cell encounters that activate T cells both during the development of the repertoire of T cells within an individual organism (positive selection; negative selection; peripheral survival) and during the control (T helper) and effector stages (T killer) of an adaptive immune response.

In the adaptive immune response, antigens are recognized by hypervariable molecules, such as antibodies or TCRs, which are expressed with sufficiently diverse structures to be able to recognize any antigen. Antibodies can bind to any part of the surface of an antigen. TCRs, however, are restricted to binding to short peptides bound to class I or class II molecules of the major histocompatibility complex (MHC) on the surface of APCs. TCR recognition of a peptide/MHC complex triggers activation (clonal expansion) of the T cell.

TCRs are heterodimers composed of two chains which can be αβ (alpha-beta) or γδ (gamma-delta). The structure of TCRs is very similar to that of immunoglobulins (Ig). Each chain has two extracellular domains, which are immunoglobulin folds. The amino-terminal domain is highly variable and called the variable (V) domain. The domain closest to the membrane is the constant (C) domain. These two domains are analogous to those of immunoglobulins, and resemble Fab fragments. The V domain of each chain has three complementarity determining regions (CDR). Proximal to the membrane, each TCR chain has a short connecting sequence with a cysteine residue that forms a disulfide bond between both chains.

Genes encoding αβ and γδ heterodimers are only expressed in the T-cell lineage. The four TCR loci (α, β, γ and δ) have a germ-line organization very similar to that of Ig. α and γ chains are produced by rearrangements of V and J segments whereas β and δ chains are produced by rearrangements of V, D, and J segments. The gene segments for TCR chains are located on different chromosomes, except the δ-chain gene segments that are between the V and J gene segments of the α chain. The location of δ-chain gene segments has a significance: a productive rearrangement of α-chain gene segments deletes C genes of the δ-chain, so that in a given cell the αβ heterodimer cannot be co-expressed with the γδ receptor.

In mice, there are about 100 Vα and 50 Jα genes segments and only one Cα segment. The δ-chain gene family has about 10 V, 2 D, and 2 J gene segments. The β-chain gene family has 20-30 V segments and two identical repeats containing 1 Dβ, 6 Jβ and 1 Cβ. Finally, the γ-chain gene family contains 7 V and 3 different J-C repeats. In humans the organization is similar to that of mice, but the number of segments varies.

The rearrangements of gene segments in α and β chains is similar to that of Igs. The α chain, like the light chain of Ig is encoded by V, J, and C gene segments. The β chain, like the heavy chain of Ig, is encoded by V, D, and J gene segments. Rearrangements of α chain gene segments result in VJ joining and rearrangements of β chain result in VDJ joining. After transcription of rearranged genes, RNA processing, and translation, the α and β chains are expressed linked by a disulfide bond in the membrane of T cells.

TCR gene segments are flanked by recognition signal sequences (RSS) containing a heptamer and a nonamer with an intervening sequence of either 12 nucleotides (one turn) or 23 nucleotides (two turn). As in Igs, enzymes encoded by recombination-activating genes (RAG-1 and RAG-2) are responsible for the recombination processes. RAG1/2 recognize the RSS and join V-J and V-D-J segments in the same manner as in Ig rearrangements. Briefly, these enzymes cut one DNA strand between the gene segment and the RSS and catalyze the formation of a hairpin in the coding sequence. The signal sequence is subsequently excised.

The combinatorial joining of V and J segments in α chains and V, D and J segments in β chains produces a large number of possible molecules, thereby creating a diversity of TCRs. Diversity is also achieved in TCRs by alternative joining of gene segments. In contrast to Ig, β and δ gene segments can be joined in alternative ways. RSS flanking gene segments in β and δ gene segments can generate VJ and VDJ in the β chain, and VJ, VDJ, and VDDJ on the δ chain. As in the case of Ig, diversity is also produced by variability in the joining of gene segments.

Hypervariable loops of the TCR known as complementarity determining regions (CDRs) recognize the composite surface made from a MHC molecule and a bound peptide. The CDR2 loops of α and β contact only the MHC molecule on the surface of APC, while the CDR1 and CDR3 loops contact both the peptide and MHC molecule. Compared with Ig, TCRs have more limited diversity in the CDR1 and CDR2. However, diversity of the CDR3 loops in TCRs is higher than that of Ig, because TCRs can join more than one D segment leading to augmented junctional diversity.

The pathogenesis of a number of autoimmune diseases is believed to be caused by autoimmune T cell responses to self-antigens present in the organism. Not all autoreactive T cells are deleted in the thymus, in contradiction with the clonal selection paradigm. Those T cells with TCRs for a broad spectrum of self-antigens represent part of the normal T-cell repertoire and naturally circulate in the periphery. It is unclear why autoreactive T cells are allowed, during their evolution, to undergo differentiation in the thymus and are accommodated in the periphery. While their physiological role is not understood, these autoreactive T cells, when activated, present a potential risk in the induction of autoimmune pathologies. Autoreactive T cells can also be isolated from normal individuals without the consequences of autoimmune diseases. It has been established that antigen recognition of autoreactivity by itself is not sufficient to mediate the autodestructive process. One of the prerequisites for autoreactive T cells to be pathogenic is that they must be activated.

Autoreactive T cells are implicated in the pathogenesis of autoimmune diseases, such as multiple sclerosis (MS) and rheumatoid arthritis (RA). The pathogenesis of autoreactive T cells in MS is generally held to arise from T cell responses to myelin antigens, in particular myelin basic protein (MBP). MBP-reactive T cells can be isolated from patients with MS but also from healthy individuals. One of the important discrepancies between myelin-reactive T cells in MS patients and those in normal individuals is the activation state of the T cells. MBP-reactive T cells are found to undergo in vivo activation, and occur at a higher precursor frequency in blood and cerebrospinal fluid in patients with MS as opposed to control individuals. These MBP-reactive T cells produce $T_H1$ cytokines, e.g. IL-2, TNFα, and γ-interferon (IFNγ), which facilitate migration of inflammatory cells into the central nervous system and exacerbate myelin-destructive inflammatory responses in MS.

Microbial infections, in particular viral infections, may play an important role in the etiology and pathogenesis of multiple sclerosis (MS). It has been speculated that MBP-reactive T cells may be activated in vivo by viral infections in patients with MS through a mechanism of molecular mimicry, which has been supported by in vitro studies. A number of viruses, including measles virus, Epstein-Barr virus and most recently human herpesvirus-6 (HHV-6), have been implicated as etiologic agents in MS based on epidemiological evidence, geographic pattern and abnormal immune response to these viruses. The potential pathologic importance of certain viral infections in MS is thought to involve direct neurotropic properties of the virus, causing tissue damage, and their ability to activate autoimmune responses directed at myelin antigens, such as MBP, through the mechanism known as molecular mimicry.

Myelin-reactive T cells have been shown to be involved in the pathogenesis of experimental autoimmune encephalomyelitis (EAE) in animals, which resembles MS. EAE can be induced actively in susceptible animals by injecting myelin proteins emulsified in an adjuvant or passively by injecting myelin-reactive T-cell lines and clones derived from myelin-sensitized animals. When activated in vitro, very small numbers of myelin-reactive T cells are required to induce EAE, while 100-fold more resting T cells with the same reactivity are incapable of mediating EAE.

EAE has been shown to be prevented and also treated by vaccination with inactivated myelin-reactive T cells, a procedure called T-cell vaccination (Ben-Nun et al., Nature, 1981; 292: 60-61). T-cell vaccination induces regulatory immune responses comprised of anti-idiotypic T cells and anti-ergotypic T cells, which lead to the depletion of myelin-reactive T cells. By depleting myelin-reactive T cells, therapeutic effects are observed in EAE and other experimental autoimmune disease models (Lider et al., Science, 1988; 239:820-822; Lohse et al. Science, 1989; 244: 820-822).

Due to the success in autoimmune disease models, T cell vaccination has recently advanced to clinical trials in patients with MS. Based on the results in experimental models such as EAE, it is believed that depletion of autoreactive T cells may improve the clinical course of MS and other autoimmune diseases.

In a pilot clinical trial, vaccination with irradiated autologous MBP-reactive T cell clones elicited $CD8^+$ cytolytic T cell responses that specifically recognized and lysed circulating MBP-reactive T cells (Zhang et al., Science, 1993; 261: 1451-1454, Medaer et al. Lancet 1995: 346:807-808). Three subcutaneous inoculations with irradiated MBP-reactive T cell clones resulted in the depletion of circulating MBP-reactive T cells in patients with MS.

In a preliminary clinical trial, circulating MBP-reactive T cells were depleted in relapsing remitting MS patients and secondary progressive MS patients (Zhang et al., J Neurol., 2002; 249:212-8), by vaccinating the patients with three subcutaneous injections of irradiated autologous MBP-reactive T cells. T cell vaccination was beneficial to each group of patients as measured by rate of relapse, expanded disability scale score and MRI lesion activity. However, there was a trend for an accelerated progression after about twelve months following the last injection. The significance of the apparent accelerated progression is unknown, but may be associated with a gradual decline of the immunity induced by T cell vaccination against MBP-reactive T cells. In approximately 10-12% of the immunized patients, MBP-reactive T cells reappeared at about the same time as the accelerated progression. In some cases, the reappearing MBP-reactive T cells originated from different clonal populations that were not detected before vaccination, suggesting that MBP-reactive T cells may undergo clonal shift or epitope spreading. Clonal shift of MBP-reactive T cells has been observed in previous studies (Zhang et al. 1995) and may be associated with the on-going disease process.

Although T cell vaccination has been demonstrated to be effective for depleting myelin-reactive T cells and potentially beneficial for MS patients, there are several problems with the treatment. T cell vaccine treatment for each patient must be individualized because the T cell receptors of myelin-reactive T cells are highly diverse and vary between different MS patients (Vandevyver et al., Eur. J. Immunol., 1995; 25:958-968, Wucherpfennig et al., J. Immunol., 1994; 152:5581-5592, Hong et al., J. Immunol., 1999; 163:3530-3538).

In addition to being individualized for each patient, up to 8 weeks is required to produce a given T cell vaccine using current procedures. Production of a T cell vaccine begins with isolating mononuclear cells from the cerebrospinal fluid (CSFMCs) or peripheral blood (PBMCs) of a patient. The isolated mononuclear cells are then cultured with myelin peptides for 7-10 days to activate myelin-reactive T cells. Cultures are then tested for specific proliferation to myelin peptides by measuring [$^3$H]-thymidine incorporation in the presence of myelin peptides over a period of 3 days. Cultures testing positive for specific proliferation to myelin peptides are then serially diluted to obtain clonal T cell lines or directly expanded. The cells are then cultured up to 6-8 weeks to expand the T cells. When the final T cell vaccine product is clonal, the T cells are homogenous with a single pattern of Vβ-Dβ-Jβ gene usage. Usually, three to six of the clonal cell lines are combined to produce a heterogeneous formulation with multiple patterns of Vβ-Dβ-Jβ gene usage. When the final T cell vaccine product is produced by direct expansion, the T cells are heterogeneous with more than one pattern of Vβ-Dβ-Jβ gene usage.

The individualized nature of T cell vaccination and the prolonged cell culture needed for production of each vaccine make treatment expensive and labor intensive under current methodologies. The extended time required for cell culture also creates a significant risk of contamination. Finally, the likelihood of clonal shift or epitope spreading of myelin-reactive T cells may require the subsequent production of a T cell vaccine for each patient with a different pattern of Vβ-Dβ-Jβ gene usage.

Therefore, there exists a need to develop improved methods of isolating T cells with specificity for antigens, such as MBP, that may be used to produce T cell vaccines for the treatment of patients with T cell-mediated diseases such as MS. There also exists a need to develop improved methods for producing T cell vaccines with a heterogeneous pattern of Vβ-Dβ-Jβ gene usage to account for clonal shift of autoreactive T cells.

In addition to vaccines based on inactivated T cells, vaccines may be based on immunogenic peptides. In EAE, encephalitogenic MBP-reactive T cells are restricted to very limited epitopes on MBP. These restrictions in the diversity of the pathogenic T-cell responses permit specific immune intervention. Various therapeutic strategies have been designed accordingly to target the Vβ region of the TCR in preventing the development of EAE in sensitized animals. For example, monoclonal antibodies have been targeted to the Vβ gene product and peptide vaccines have been based on the CDR2 region of the responsible Vβ gene.

Some of the studies on EAE have been extended to human autoimmune diseases. For instance, a peptide corresponding to TCR Vβ 5.2 has been used in clinical trials to treat patients with MS and a Vβ 14 peptide has been used to vaccinate patients with RA. U.S. Pat. No. 5,614,192 (Vandenbark) discloses treatment of autoimmune diseases by the use of immunogenic TCR peptides of 15 to 30 amino acids comprising at least part of CDR2. U.S. Pat. No. 6,303,314 (Zhang) discloses the treatment of autoimmune diseases by using certain immunogenic TCR peptides in combination with immunogenic T cell activation marker peptides.

One area in which vaccination with TCR peptides can be improved is by determining which, if any, common motifs are found in the autoreactive TCRs of a patient with an autoimmune disease such as MS. Such common motifs can be used either as a basis for a peptide vaccine to activate an anti-idiotypic immune response in MS patients for the purpose of depleting T cells which have TCRs comprising said motifs, or as a target for the preparation of antibodies that can functionally block or directly deplete T cells which have TCRs comprising said motifs.

Therefore, it is desirable to determine the amino acid sequences of common motifs specifically found in the TCRs of autoreactive T cells from patients with autoimmune diseases. It is also desirable to be able to readily detect such motifs in a patient sample by a convenient method, such as PCR. In addition, it is desirable to use peptides identical to or derived from the detected motifs to treat patients with the autoimmune disease. It is also desirable to use antibodies which specifically bind to said motifs to treat a patient with an autoimmune disease.

U.S. Pat. No. 6,303,314 (Zhang) discloses such a common motif found in the TCRs of a subset of Vβ13.1 T cells, the "LGRAGLTY motif", which has the amino acid sequence Leu Gly Arg Ala Gly Leu Thr Tyr (SEQ ID NO: 10), as well as a method for its ready detection by PCR. This motif is found in some TCRs of some autoreactive T cells that recognize amino acids 83-99 of MBP (hereinafter "MBP83-99"). Peptides based on the LGRAGLTY motif can be used to vaccinate some patients in order to treat or prevent autoimmune diseases with which Vβ13.1-LGRAGLTY is associated (e.g., MS). U.S. Provisional Patent No. 60/386,287 (Zhang) discloses an additional three motifs present in the TCRs of MBP-reactive T cells.

As autoreactive T cells associated with autoimmune diseases, such as MS, may be activated by foreign antigens that mimic self-antigens, such as MBP, there remains a need to identify other TCR sequences, including CDR sequences, that cross-react with a self-antigen and a foreign antigen mimicking said self-antigen. In addition, there remains a need to be able to detect TCR sequences, including CDR sequences, which are expressed by MBP-reactive T cells that cross-react with a self-antigen and a foreign antigen mimicking said self-antigen. Finally, there remains a need to develop treatments for autoimmune diseases associated with TCR sequences, and more particularly CDR sequences, expressed by MBP-reactive T cells that cross-react with a self-antigen and a foreign antigen mimicking said self-antigen.

SUMMARY

The present invention is generally directed to methods of isolating cross-reactive T cells and more particularly T cells specific for a self-antigen and also a foreign antigen. The methods for isolating a cross-reactive T cell comprises incubating a sample comprising T cells with an antigen that comprises an epitope present in the self-antigen and the foreign antigen, and optionally one or more autoantigens. The T cell may also be isolated by selecting T cells that express one or more first markers selected from the group consisting of CD69, CD4, CD25, CD36 and HLADR; and one or more second markers selected from the group consisting of IL-2, IFNγ, TNFα, IL5, IL-10 and IL-13.

The methods of the invention are particularly useful for isolating cross-reactive T cells which play a role in the pathogenesis of autoimmune diseases.

The methods of the invention also permit the diagnosis of autoimmune disease as well as monitoring the progression of the disease and for monitoring the efficacy of treatments for the disease.

The methods of the invention also allow the preparation of autologous T cell vaccines for the treatment of T cell related autoimmune diseases.

The methods for vaccine preparation generally involve the isolation of cross-reactive T cells as described above optionally followed by subsequent culturing steps which allows the expansion of the population of isolated cross-reactive T cells.

The invention inter alia is also directed to T cell vaccines and pharmaceutical compositions comprising cross-reactive T cells isolated using the methods of the invention.

The methods of the invention are also useful for characterizing cross-reactive T cell receptors and their encoding nucleic acids.

DETAILED DESCRIPTION

1. Definitions

To aid in the understanding of the present invention, several terms are defined below.

"Autoantigen" or "self-antigen" as used herein refers to an immunogenic antigen or epitope which is native to a mammal and which may be involved in the pathogenesis of an autoimmune disease.

"CD," "cluster of differentiation" or "common determinant" as used herein refers to cell surface molecules recognized by antibodies. Expression of some CDs is specific for cells of a particular lineage or maturational pathway, and the expression of others varies according to the state of activation, position, or differentiation of the same cells.

"Derived from" or "a derivative thereof," in the context of nucleotide sequences means that the nucleotide sequence is not limited to the specific sequence described, but also includes variations in that sequence, which may include nucleotide additions, deletions, substitutions, or modifications to the extent that the variations to the described sequence retain the ability to hybridize under moderate or highly stringent conditions to the complement of the described sequence. In the context of peptide or polypeptide sequences, "derived from" or "a derivative thereof" means that the peptide or polypeptide is not limited to the specific sequence described, but also includes variations in that sequence, which may include amino acid additions, deletions, substitutions, or modifications to the extent that the variations in the listed sequence retain the ability to elicit an immune response to the described sequence.

"Immunogenic," when used to describe a peptide or polypeptide, means the peptide or polypeptide is able to induce an immune response, either T cell mediated, antibody, or both.

"Immune-related disease" means a disease in which the immune system is involved in the pathogenesis of the disease. A subset of immune-related diseases are autoimmune diseases. Autoimmune diseases include, but are not limited to, rheumatoid arthritis, myasthenia gravis, multiple sclerosis, psoriasis, systemic lupus erythematosus, autoimmune thyroiditis (Hashimoto's thyroiditis), Graves' disease, inflammatory bowel disease, autoimmune uveoretinitis, polymyositis, and certain types of diabetes. In view of the present disclosure, one skilled in the art can readily perceive other autoimmune diseases treatable by the compositions and methods of the present invention.

"PCR" means the polymerase chain reaction, for example, as generally described in U.S. Pat. No. 4,683,202 (issued Jul. 28, 1987 to Mullis), which is hereby incorporated by reference in its entirety. PCR is an amplification technique wherein selected oligonucleotides, or primers, may be hybridized to nucleic acid templates in the presence of a polymerization agent (such as a DNA or RNA polymerase) and nucleotide triphosphates, whereby extension products may be formed from the primers. These products may then be denatured and used as templates in a cycling reaction that amplifies the number and amount of existing nucleic acids which may facilitate their subsequent detection. A variety of PCR techniques are known in the art and may be used in connection with the disclosure herein.

"Peptide" or "polypeptide" is a linked sequence of amino acids and may be natural, synthetic, or a modification or combination of natural and synthetic.

"Primer" means an oligonucleotide, whether natural, synthetic, or a modification thereof, capable of acting as a point of initiation of nucleotide synthesis sufficiently complementary to a specific nucleotide sequence on a template molecule.

"Probe" means an oligonucleotide, whether natural, synthetic, or a modification thereof, capable of specifically binding to a sufficiently complementary nucleotide sequence.

"T cell mediated disease" means a disease arising as a result of T cells recognizing self-antigens.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Isolation of Cross-Reactive T Cells

T cells may be activated and expanded in cell culture by incubation with an antigen target and optionally antigen presenting cells. Once activated, T cells undergo a complex cascade of cell signaling which leads to the transcription and expression of many gene products. The invention described herein takes advantage of gene products specific for activated T cells for the identification and isolation of T cells with desired antigen specificity.

In a first aspect, the present invention is directed to a method for isolating a T cell that cross-reacts with a self-antigen and a foreign antigen. A sample comprising T cells is incubated with an antigen that comprises an epitope present in the self-antigen and the foreign antigen, thereby causing the activation of a T cell that cross-reacts with the self-antigen and the foreign antigen. The sample may be incubated with antigen under conditions as described in U.S. patent application Ser. No. 09/952,532 (Zhang) and U.S. Provisional Patent No. 60/405,521 (Zhang), which are hereby incorporated by reference in their entirety.

A cross-reactive T cell may then be isolated by cloning or direct expansion as described in U.S. patent application Ser. No. 09/952,532 (Zhang). A cross-reactive T cell may also be isolated by selecting for T cells that express gene products of T cells activated as described in U.S. Provisional Patent No. 60/405,521 (Zhang). Isolated cross-reactive T cells may have a homogeneous or heterogeneous pattern of Vβ-Dβ-Jβ gene usage. The isolated cross-reactive T cells may be enriched by at least 90%, 95%, 98% or 99.5% from whole blood.

T cells comprising a homogenous pattern of Vβ-Dβ-Jβ gene usage may be used to formulate a monoclonal T cell vaccine as described in U.S. Provisional Patent No. 60/405, 521 (Zhang). T cells comprising a heterogeneous pattern of Vβ-Dβ-Jβ gene usage may be used to formulate a polyclonal T cell vaccine as described in U.S. Provisional Patent No. 60/405,521 (Zhang), which may prevent epitope spreading in vaccinated patients.

The self-antigen may be myelin basic protein or a fragment, variant, analog, homolog or derivative thereof. The self-antigen may also be a fragment of MBP of between 4 and 50 amino acids that comprises residues 96-102 of myelin basic protein or a fragment, variant, analog, homolog or derivative thereof. The fragment of MBP may be 4, 6, 8, 10, 12, 15, 20, 25, 30, 35, 40, 45 or 50 amino acids. The self-antigen may also be a fragment of MBP comprising amino acids 93-105 or a fragment, variant, analog, homolog or derivative thereof. The self-antigen may also be a peptide consisting of amino acids 93-105 of MBP or a fragment, variant, analog, homolog or derivative thereof.

The foreign antigen may be human herpesvirus-6 U24 or a fragment, variant, analog, homolog or derivative thereof. The foreign may also be a fragment of HHV-6 (U24) of between 4 and 50 amino acids that comprises residues 4-10 of HHV-6 (U24) or a fragment, variant, analog, homolog or derivative thereof. The fragment of HHV-6 (U24) may be 4, 6, 8, 10, 12, 15, 20, 25, 30, 35, 40, 45 or 50 amino acids. The foreign antigen may also be a fragment of HHV-6 (U24) comprising amino acids 1-13 or a fragment, variant, analog, homolog or derivative thereof. The foreign antigen may also be a peptide consisting of amino acids 1-13 of HHV-6 (U24) or a fragment, variant, analog, homolog or derivative thereof.

HHV-6 has predominant tropism for $CD4^+$ T cells. It is the etiologic agent for infantile exanthem. Common to other herpesviruses, latency of HHV-6 is established after primary infection and its genomic material can be found in T cells of healthy adults. HHV-6 infection can re-activate under certain conditions, such as in immuno-compromised patients. Expression of HHV-6 virion proteins has been found in oligodendrocytes obtained from patients with MS. More recent studies have demonstrated higher titers of antibodies to HHV-6 and cell-free DNA of HHV-6 in sera and cerebrospinal fluid of MS patients, suggesting re-activation of HHV-6 in MS while other studies have reported conflicting results. Interestingly, a viral protein of both variant A and variant B of HHV-6, designated U24, shares significant amino acid sequence homology with MBP. There is a stretch of 7 identical amino acids within residues 4-10 of HHV-6 U24 antigen and residues 96-102 of human MBP, raising the possibility that MBP-reactive T cells may be susceptible to activation by the HHV-6 viral antigen sharing the sequence homology.

The cross-reactive T cells may be present in any sample comprising mononuclear cells. The sample may be isolated from the peripheral blood or cerebral spinal fluid of an MS patient or from the synovial fluid of a RA patient. T cells from patients with other autoimmune diseases may be similarly isolated from peripheral blood and/or tissues involved with the disease. Mononuclear cells may be enriched in the sample by using centrifugation techniques known to those in the art including, but not limited to, Ficoll® gradients.

In a second aspect, the present invention is directed to a T cell that cross-reacts with a self-antigen and foreign antigen isolated by the method of the first aspect of the present invention.

In a third aspect, the present invention is directed to a method for isolating a T cell that cross-reacts with a self-antigen and a foreign antigen together with T cells that are specific for one or more antigens of interest. Similar to the method of the first aspect of the present invention, a sample comprising T cells is incubated with an antigen that comprises an epitope present in the self-antigen and the foreign antigen together with with one or more other antigens, thereby causing the activation of a T cell that cross-reacts with the self-antigen and the foreign antigen and the activation of T cells specific for the one or more other antigens.

The one or more other antigens may be autoantigens. The autoantigen may be myelin basic protein (MBP), proteolipid protein (PLP), myelin oligodendrocyte glycoprotein (MOG), or a fragment thereof. The autoantigen may also be an immunodominant fragment including, but not limited to, residues 83-99 or residue 151-170 of MBP. The one or more other antigens may also be any immunogen which is capable of eliciting an immune response to MBP, PLP, MOG, or a fragment and/or derivative thereof. When the one or more other antigens are an autoantigen, the activated T cells may be autoreactive T cells.

The T cells may have a heterogeneous pattern of $V\beta$-$D\beta$-$J\beta$ gene usage that express different TCRs which are each specific for the self-antigen or the antigen of interest. The T cells may also have a heterogeneous pattern of $V\beta$-$D\beta$-$J\beta$ gene usage that express different TCRs which are specific for more than one antigen of interest. T cells comprising a heterogeneous pattern of $V\beta$-$D\beta$-$J\beta$ gene usage may be used to formulate a polyclonal T cell vaccine as described in U.S. Provisional Patent No. 60/405,521 (Zhang), which may prevent epitope spreading in vaccinated patients.

In a fourth aspect, the present invention is directed to a T cell that cross-reacts with a self-antigen and foreign antigen together with T cells that are specific for one or more antigens of interest isolated by the method of the third aspect of the present invention.

3. Quantifying the Number of Antigen-Specific T Cells

In a fifth aspect, the present invention is directed to a method of determining the relative frequency of cross-reactive T cells in a sample by determining the number of T cells isolated by the method of the first or third aspects of the present invention.

4. Diagnosing an Autoimmune Disease

In a sixth aspect of the present invention, a patient with an autoimmune disease may be diagnosed by obtaining a sample from a patient and isolating cross-reactive T cells by the method of the first or third aspects of the present invention. The autoimmune disease may be diagnosed by comparing the level of cross-reactive T cells and optionally other autoreactive T cells in a patient to a control. The level of cross-reactive T cells may be determined in accordance with the method of the fifth aspect of the present invention.

5. Monitoring the Progress of an Autoimmune Disease

In a seventh aspect of the present invention, an autoimmune disease may be monitored by determining the frequency of cross-reactive T cells and optionally other autoreactive T cells in a sample from a patient with an autoimmune disease in accordance with the fifth aspect of the present invention. The severity of symptoms of the autoimmune disease may correlate with the number of cross-reactive T cells and optionally other autoreactive T cells. In addition, an increase in the number of cross-reactive T cells and optionally other autoreactive T cells in the sample may be used as an indication to apply treatments intended to minimize the severity of the symptoms and/or treat the disease before the symptoms appear.

6. Producing a Vaccine for the Treatment of an Autoimmune Disease

In an eighth aspect of the present invention, a composition may be produced for treating an autoimmune disease by inactivating-cross-reactive T cells and optionally other autoreactive T cells which have been isolated (and optionally expanded in culture as described herein) by the method of the first or third aspects of the present invention. The cross-reactive T cells and optionally other autoreactive T cells may be inactivated using a number of techniques known to those in the art including, but not limited to, chemical inactivation or irradiation. The cross-reactive T cells and optionally other autoreactive T cells may be preserved either before or after inactivation using a number of techniques known to those in the art including, but not limited to, cryopreservation. As described below, the composition may be used as a vaccine to deplete cross-reactive T cells and optionally other autoreactive T cells in autoimmune patients.

The composition may be a pharmaceutical composition, which may be produced using methods well known in the art. Pharmaceutical compositions used as preclinical and clinical therapeutics in the treatment of disease or disorders may be produced by those of skill, employing accepted principles of diagnosis and treatment. Such principles are known in the art, and are set forth, for example, in Braunwald et al., eds., Harrison's Principles of Internal Medicine, 11th Ed., McGraw-Hill, publisher, New York, N.Y. (1987), which is hereby incorporated by reference in its entirety. The pharmaceutical composition may be administered to any animal which may experience the beneficial effects of the composition. Animals receiving the pharmaceutical composition may be humans or other mammals.

a. Vaccine

In a ninth aspect, the present invention is drawn to a composition produced by the method of the eighth aspect of the present invention. The composition may be a vaccine, which may be used to deplete cross-reactive T cells and optionally autoreactive T cells in autoimmune patients.

7. Treatment of an Autoimmune Disease

In a tenth aspect, an autoimmune disease may be treated in patients with cross-reactive T cells and optionally autoreactive T cells by administering a composition according to the ninth aspect of the present invention. The composition may be a vaccine, which may lead to the depletion of cross-reactive T cells and optionally autoreactive T cells in the patient.

A vaccine may comprise autoreactive T cells comprising homogeneous ("monoclonal") or heterogeneous ("polyclonal") patterns of Vβ-Dβ-Jβ gene usage. Clinical studies indicate that autoimmune patients receiving autologous monoclonal T cell vaccination may show a gradual decline in the immunity against myelin-reactive T cells. In some cases, the reappearing autoreactive T cells may originate from different clonal populations, suggesting that myelin-reactive T cells may undergo clonal shift or epitope spreading potentially associated with the ongoing disease process. Clonal shift or epitope spreading may be a problem in autoimmune diseases mediated by autoreactive T cells. A vaccine comprising polyclonal autoreactive T cells capable of depleting multiple populations of autoreactive T cells may avoid problems with clonal shift or epitope spreading.

The composition may be a pharmaceutical composition, which is administered by any means that achieve their intended purpose. For example, administration may be by parenteral, subcutaneous, intravenous, intraarterial, intradermal, intramuscular, intraperitoneal, transdermal, transmucosal, intracerebral, intrathecal, or intraventricular routes. Alternatively, or concurrently, administration may be by the oral route. The pharmaceutical compositions may be administered parenterally by bolus injection or by gradual perfusion over time.

The dosage administered may be dependent upon the age, sex, health, and weight of the recipient, kind of concurrent treatment, if any, frequency of treatment, and the nature of the effect desired. The dose ranges for the administration of the pharmaceutical compositions may be large enough to produce the desired effect, whereby, for example, autoreactive T cells are depleted, as measured by the seventh aspect of the present invention, is achieved, and the autoimmune disease is significantly prevented, suppressed, or treated. The doses may not be so large as to cause adverse side effects, such as unwanted cross reactions, generalized immunosuppression, anaphylactic reactions and the like.

The pharmaceutical compositions may further comprise suitable pharmaceutically acceptable carriers comprising excipients and auxiliaries which may facilitate processing of the active compositions into preparations which can be used pharmaceutically Additives to the pharmaceutical compositions may include the inclusion of an adjuvant, such as alum, chitosan, or other adjuvants known in the art. (See, for example, Warren et al., Ann. Rev. Immunol. 4:369-388 (1986); Chedid, L., Feder. Proc. 45:2531-2560 (1986), which are hereby incorporated by reference in their entirety). The pharmaceutical compositions may also further comprise liposomes to enhance delivery or bioactivity, using methods and compounds known in the art.

Suitable formulations for parenteral administration include aqueous solutions of the inactivated autoreactive T cells, for example, water-soluble salts in aqueous solution. In addition, oil suspensions comprising inactivated autoreactive T cells may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. The suspension may also contain stabilizers.

The inactivated cross-reactive T cells and optionally autoreactive T cells may be formulated using conventional pharmaceutically acceptable parenteral vehicles for administration by injection. These vehicles may be nontoxic and therapeutic, and a number of formulations are set forth in Remington's Pharmaceutical Sciences, (supra). Nonlimiting examples of excipients are water, saline, Ringer's solution, dextrose solution and Hank's balanced salt solution. Pharmaceutical compositions may also contain minor amounts of additives such as substances that maintain isotonicity, physiological pH, and stability.

The inactivated cross-reactive T cells and optionally autoreactive T cells may be formulated at total cell concentrations including from about $5 \times 10^2$ cells/ml to about $1 \times 10^9$ cells/ml. Preferred doses of the inactivated autoreactive T cells for use in preventing, suppressing, or treating an autoimmune disease may be in the range of about $2 \times 10^6$ cells to about $9 \times 10^7$ cells.

8. Determination of TCR Repertoire

In an eleventh aspect, the present invention is drawn to a method of determining the repertoire of nucleic acids encoding one or more T cell receptors, or a portion thereof, in an autoimmune patient by amplifying nucleic acids encoding one or more T cell receptors from T cells isolated by the first or third aspects of the present invention, wherein said amplification is performed using a primer pair. The first primer of the primer pair may be an oligonucleotide of about 15 to 30 nucleotides in length that hybridizes to a nucleic acid comprising the variable region of the TCR gene. The second primer of the primer pair may be an oligonucleotide of about 15 to 30 nucleotides in length that hybridizes to a nucleic acid comprising the constant region of the TCR gene. The primer pair may be used to amplify a nucleic acid that hybridizes to the Vβ-Dβ-Jβ region of the TCR gene.

Nucleic acids encoding one or more T cell receptors from T cells (the "Target Sequence") or a fragment thereof may be amplified from a sample by the polymerase chain reaction (PCR) using any particular PCR technique or equipment known in the art. For example, PCR amplification may follow a procedure wherein a reaction mixture is prepared that contains the following ingredients: 5 μL 10×PCR buffer II (100 mM Tris-HCl, pH 8.3, 500 mM KCl), 3 μL 25 mM $MgCl_2$, 1 μL 10 mM dNTP mix, 0.3 μL Taq polymerase (5 U/μL) (AmpliTaq Gold, Perkin Elmer, Norwalk, Conn.), 30 pmol of a first primer, 30 pmol of a second primer, and 1 μL of sample DNA. The polymerase may be stable at temperatures of at least 95° C., have a processivity of 50-60 and have an extension rate of greater than 50 nucleotides per minute.

The PCR reaction may be performed with an amplification profile of 1 min at 95° C. (denaturation), 20 sec at 56° C. (annealing), and 40 sec at 72° C. (extension) for a total of 40 cycles. Before the first cycle begins, the reaction mixture may undergo an initial denaturation for a period of about 5 min to 15 min. Similarly, after the final cycle is complete, the reaction mixture may undergo a final extension for a period of about 5 min to 10 min. Certain PCR reactions may work with as few as 15 to 20 cycles or as many as 50 cycles. Depending upon the specific PCR reaction, longer or shorter incubation times and higher or lower temperatures for each step of the amplification profile may be used.

The sample comprising the Target Sequence, may be a nucleic acid, such as genomic DNA, cDNA, DNA previously amplified by PCR, or any other form of DNA. The sample may be isolated, directly or indirectly, from any animal or human tissue comprising T cells, such as peripheral blood mononuclear cells (PBMC). Genomic DNA may be isolated directly from a tissue comprising T cells. cDNA may be isolated indirectly by reverse transcription of mRNA directly isolated from a tissue comprising T cells.

The ability to detect the Target Sequence may be enhanced by isolating the sample DNA indirectly by amplification of genomic DNA, cDNA, or any other form of DNA, by a two-step PCR reaction. For example, a first PCR amplification reaction may be performed to amplify a preliminary fragment that is larger than, and comprises, a fragment to which the first and second primers are capable of selectively binding on opposite strands. A second PCR amplification reaction may then be performed, using the preliminary fragment as a template with the first and second primers, to amplify a fragment comprising the Target Sequence. If either the first or second primer is used in the first PCR reaction to amplify the preliminary fragment, the second PCR reaction is "semi-nested." If neither the first or second primer is used in the first PCR reaction to amplify the preliminary fragment, the second PCR reaction is "nested."

In an exemplary two-step PCR reaction, one or more nucleic acids encoding one or more T cell receptors from T cells may be amplified by performing a first PCR reaction using a first preliminary primer that anneals to the Vβ region of the TCR gene and a second preliminary primer that anneals to the Cβ region of the TCR gene, which amplifies a preliminary fragment that extends from Vβ through the Vβ-Dβ-Jβ junction to Cβ, followed by a second PCR reaction which may be nested or semi-nested. In light of the present disclosure, the skilled artisan will be able to select appropriate primers and reaction conditions for PCR amplification of the Target Sequence.

After amplification of the Target Sequence, the amplified product may be detected by a number of procedures. For example, an aliquot of amplification product may be loaded onto an electrophoresis gel, to which an electric field is applied to separate DNA molecules by size. In another method, an aliquot of amplification product may be loaded onto a gel stained with SYBR green, ethidium bromide, or another molecule that will bind to DNA and emit a detectable signal. A dried gel may contain a labeled oligonucleotide that hybridizes to the Target Sequence, from which an autoradiograph may be taken by exposing the gel to film.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

9. Peptides

In a twelfth aspect, the present invention is directed to a peptide comprising about 4 to 50 amino acids in length, comprising at least 4 contiguous amino acids of the V-D-J sequences shown on Table 2 (SEQ ID NOS: 1-6), or sequences derived therefrom. The peptide may also be about 4 to 12 amino acids in length, comprising either 4, 5, 6, 7, 8, 9, 10, 11 or 12 contiguous amino acids of SEQ ID NOS: 1-6, or sequences derived therefrom. The peptide may also be about 4 to 20 amino acids in length, comprising sequence from SEQ ID NOS: 1-6, or sequences derived therefrom. The peptide may be natural, synthetic, or derived therefrom.

The peptide may be used as an antigen to elicit an immune response to a peptide or polypeptide comprising sequence from SEQ ID NOS: 1-6, or sequences derived therefrom. As described in U.S. Provisional Patent No. 60/386,287 an immune response elicited by the peptide may be used as a basis for the production of a vaccine, the prevention and treatment of an autoimmune disease, the production of antibodies, the purification of antibodies, and in diagnostic assays.

10. Prevention of MS

In a thirteenth aspect, an autoimmune disease such as MS may be prevented in patients infected with HHV-6 by administering an antiviral agent that eliminates or reduces reactivation of latent HHV-6 and optionally the composition comprising autoreactive T cells produced by the method of the eighth aspect of the present invention or a composition comprising one or more peptides of the twelfth aspect of the present invention, or a combination thereof. Antiviral agents are well known in the art, including nucleoside analogs and interferon.

Example 1

Precursor Frequency of Cross-Reactive T Cells in MS Patients

Twelve MS patients were included in the study. All patients were characterized as having relapsing-remitting or secondary progressive MS for more than two years. They were not treated with immunosuppressive agents or immunomodulatory agents (e.g. beta-interferon or Glatiramer Acetate) for at least 3 months prior to the enrollment in the study and throughout the study. Informed consent was obtained from the patients after explaining the experimental procedures. Eleven asymptomatic healthy volunteers were included as control subjects. As has been previously reported, a higher incidence of serum cell-free HHV-6 viral DNA was detected in this group of MS patients than that in healthy controls (Table 1).

The T cell responses to two synthetic peptides containing an identical core sequence of seven amino acids was measured to estimate the precursor frequency of cross-reactive T cells in PBMC. Two 13-mer peptides corresponding to residues 1-13 of HHV-6 U24 and residues 93-105 of MBP were synthesized and purified to greater than 95%. The MBP$_{93-105}$ and HHV-6 (U24)$_{1-13}$ peptides contain the identical core sequence of 7 amino acids with distinct flanking residues (MBP-IVTPRTPPPSQGK and HHV6-MDRPRTPPPSYSE) (SEQ ID NO: 8 and SEQ ID NO: 9, respectively).

Peripheral blood mononuclear cells (PBMC) were seeded at 3×10$^5$ cells per well in 96-well U-bottomed plates in the presence of the peptides of MBP$_{93-105}$ or HHV-6 (U24)$_{1-13}$ at 30 μg/ml or the whole MBP (40 μg/ml), respectively. A total of 24 wells were plated for each antigen. Seven days later, the cultures were tested for the reactivity to both peptides using AIM-V serum free medium (Gibco BRL, Grand Island, N.Y.) alone as a control. To this end, each culture was split into three identical aliquots and tested for the reactivity to MBP and the indicated peptides in duplicate. Two aliquots were tested for reactivity to peptide MBP$_{93-105}$ and peptide HHV-6 (U24)$_{1-13}$ at the same concentration of 30 μg/ml, respectively, in the presence of irradiated (6,000 rads) autologous PBMC (10$^5$ cells per well) as a source of antigen-presenting cells (APC). One aliquot served as a control (medium alone in the presence of APC). The reactivity of the end cultures was measured after 72 hours by proliferation assays as described in Zhang et al., "MHC restricted clonotypic depletion of human myelin basic protein by T cell vaccination," Science 261:1451-1454 (1993), which is hereby incorporated by reference in its entirety.

According to the reactivity of the resulting T cells, they were categorized as mono-specific T cells or cross-reactive T cells. Mono-specific MBP- or HHV-6 reactive T cells were reactive only to the peptide originally used to prime the cells. Mono-specific T cells were defined as reactive to the given peptide when CPM was greater than 1,000 and exceeded CPM of the control (medium alone) and of the other peptide by at least three-fold. Cross-reactive T cells were reactive to both peptides after being originally primed with only one of the peptides. Cross-reactive T cells were defined as CPM of both peptides exceeded 1,000 and the control CPM by at least three-fold. The frequency of peptide-reactive T cells was then estimated by dividing the number of positive wells by the total number of PBMC seeded in the initial culture.

Figure 1:
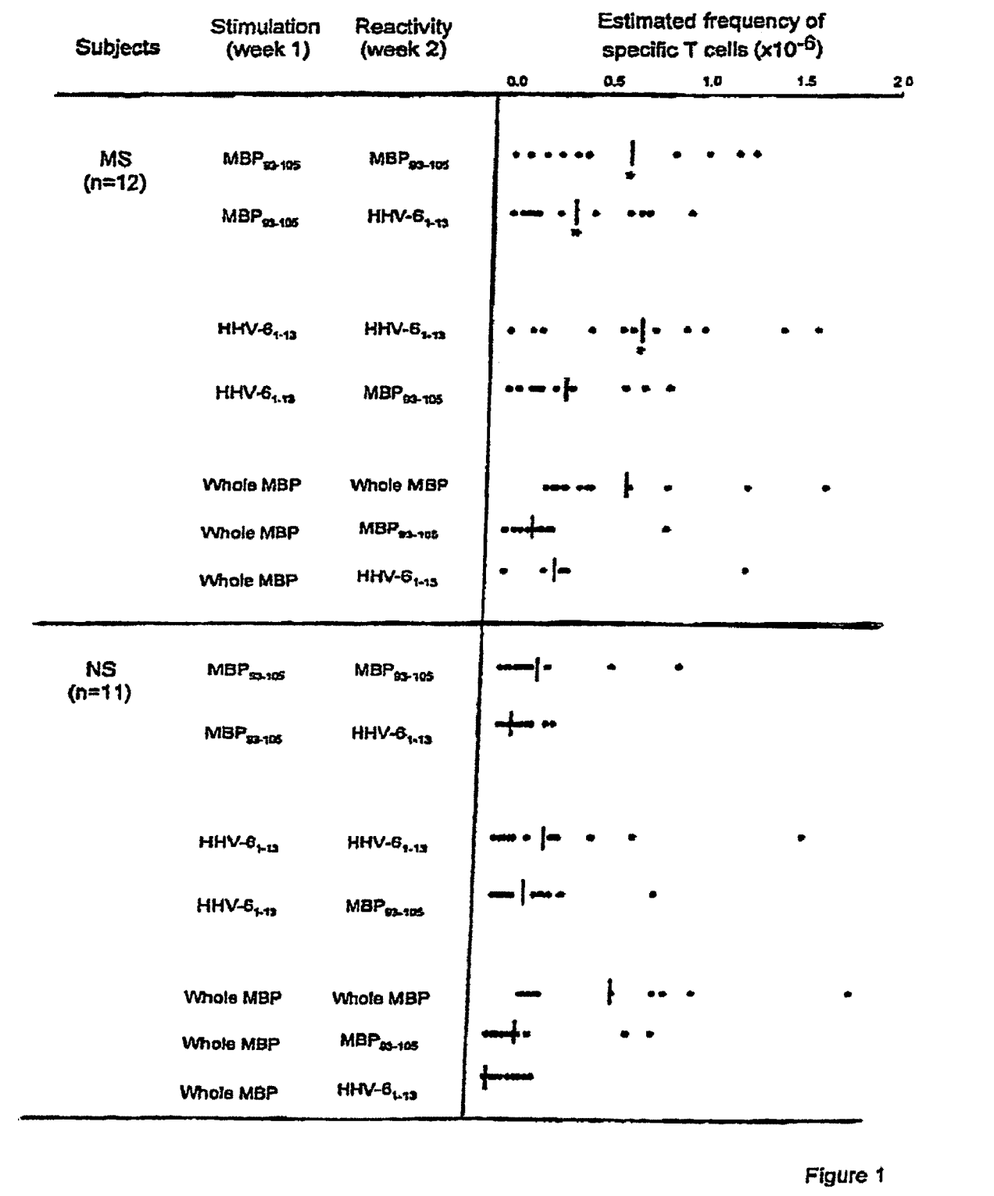
FIG. 1 demonstrates the T cell responses to the $MBP_{93-105}$ and $HHV-6 (U24)_{1-13}$ peptides in MS patients and healthy controls. The circles represent the individual precursor frequency and the bars indicate the mean precursor frequency of the T cells within the group. The asterisks indicate statistically significant differences ($p<0.05$) between the MS group and the control group.

As shown in FIG. 1, although T cells recognizing the whole MBP occurred at a similar estimated frequency (0.6×10$^{-6}$ in PBMC) in MS patients and healthy subjects, the estimated frequency of T cells specific for the two peptides was significantly higher in MS patients than that of healthy controls (0.53×10$^{-6}$ VS. 0.19×10$^{-6}$ for peptide MBP$_{93-105}$ and 0.7× 10$^{-6}$ vs. 0.32×10$^{-6}$ for peptide HHV-6 (U24)$_{1-13}$, p<0.05). The estimated frequency of the cross-reactive T cells primed by peptide HHV-6 (U24)$_{1-13}$ was 0.30×10$^6$ in MS patients, which represented greater than 50% of all T cells recognizing peptide MBP$_{93-105}$ in the MS cohort (FIG. 1). T cells reactive to both peptides were also present but at significantly lower precursor frequency (0.17×10$^{-6}$) in healthy controls. Similarly, the cross-reactive T cells were also detected in cultures primed with peptide MBP$_{93-105}$ in MS patients as well as in control subjects (0.36×10$^{-6}$ vs. 0.09×10$^{-6}$, p<0.05). Consistent with these observations was the increased frequency of T cells that were initially primed with the whole MBP and reacted to peptide HHV-6 (U24)$_{1-13}$ in patients with MS compared to the control group (0.33×10$^{-6}$ vs. 0.05×10$^{-6}$) but the difference was not statistically significant (p=0.08). Furthermore, there was no correlation between the detection of HHV-6 DNA and the specific T cell frequencies. Taken together, the results suggest that a significant fraction of T cells recognizing the 93-105 region of MBP could be fully activated to proliferate by peptide HHV-6 (U24)$_{1-13}$ that shares the sequence homology with the MBP peptide.

Example 2

Cytokine Profile and Phenotypic Expression

The cytokine profile was determined for mono-specific and cross-reactive T cells lines derived from the T cells of Example 1. T cell lines were cloned under limiting dilution conditions in the presence of PHA (Sigma, St. Louis Mo.) and irradiated autologous PBMC as accessory cells. Briefly, T cells were plated out at 0.3 cell per well under limiting dilution conditions and cultured with 10$^5$ irradiated autologous PBMC and 5 μg/ml PHA. Cultures were fed with fresh medium containing 50 IU/ml rIL-2 Boehringer Mannheim, Indianapolis, Ind.) every 4 days. After approximately 10-12 days, growth-positive wells became visible and were tested in proliferation assays for proliferative responses to the peptides. A total of 67 lines were produced from MS patients and 38 lines from control subjects.

The cytokine profile of the resulting T cell lines was determined quantitatively using ELISA kits (PharMingen, San Diego, Calif.). Microtiter plates (96-wells, NUNC Maxisorp) were coated overnight at 4° C. with 1 μg/well of a purified mouse capturing monoclonal antibody to human cytokine (IL-4, IL-10, TNF-α, γ-IFN) (PharMingen). Plates were washed and non-specific binding sites were saturated with 10% (w/v) fetal bovine serum (FBS) for 1 hour and subsequently washed. Supernatants and cytokine standards were diluted with PBS and added in duplicate wells. Plates were incubated at 37° C. for 2 hr and subsequently washed with PBS-T. Matched biotinylated detecting antibody were added to each well and incubated at room temperature for 2 hours. After washing, avidin-conjugated horseradish peroxidase was added and plates were incubated for 1 hour. 3,3',5,5'-tetramethylbenzidine (TMB, Sigma) was used as a substrate for color development. Optical density was measured at 450 nm using an ELISA reader (Bio-Rad Laboratories, Hercules, Calif.) and cytokine concentrations were quantitated by Microplate computer software (Bio-rad) using a double eight-point standard curve.

Figure 2:
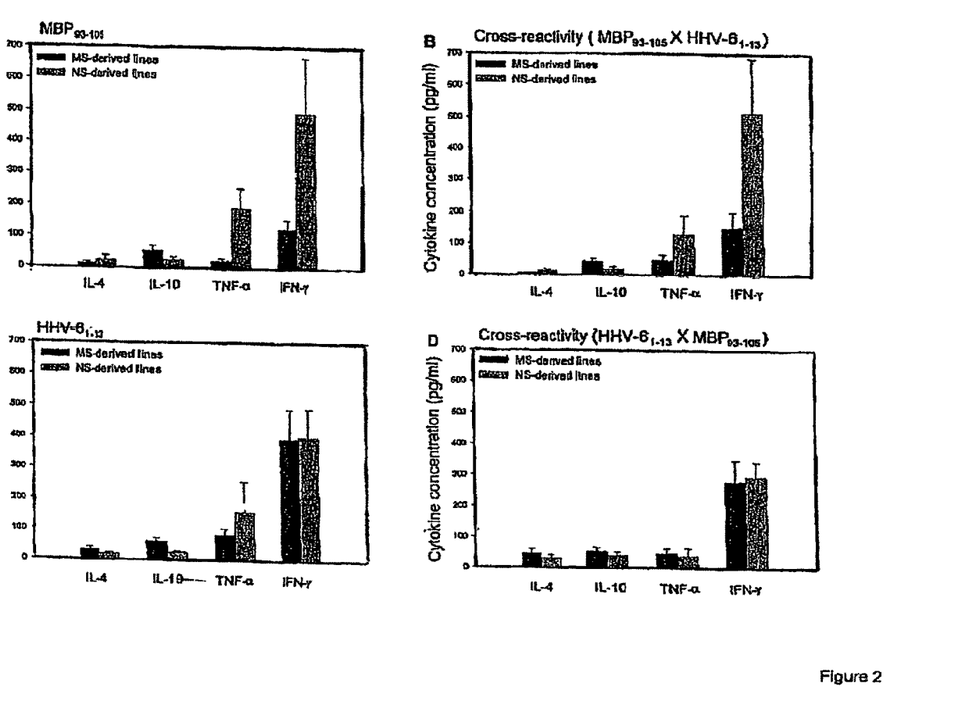
FIG. 2 demonstrates cytokine concentrations produced by mono-specific and cross-reactive T cells after challenge with the $MBP_{93-105}$ and $HHV-6 (U24)_{1-13}$ peptides. Panel A shows the cytokine profile of the T cell lines primed with peptide $MBP_{93-105}$ and challenged with the same peptide in week 2. Panel B shows the cytokine profile of the cross-reactive T cell lines primed with peptide $MBP_{93-105}$ and challenged with peptide $HHV-6 (U24)_{1-13}$ in week 2. Panel C shows the cytokine profile of the T cell lines primed with peptide HHV-6 (U24)$_{1-13}$ and challenged with the same peptide in week 2. Panel D shows the cytokine profile of cross-reactive T cell lines primed with peptide HHV-6 (U24)$_{1-13}$ and challenged with peptide MBP$_{93-105}$ in week 2.

As illustrated in FIG. 2, overall the T cell lines examined were predominantly of Th1 phenotype, producing predominantly γ-IFN, various amounts of TNF-α but not IL-4 and IL-10, regardless of their peptide specificity. However, MS-derived T cell lines specific for peptide $MBP_{93-105}$ as well as the cross-reactive T cell lines initially primed by peptide $MBP_{93-105}$ differed considerably in the production of γ-IFN and TNF-α from those generated from control subjects. In general, the cross-reactive T cell lines exhibited similar cytokine profile as those specific for the same peptide by which the cross-reactive T cell lines were initially primed (FIG. 2B vs. 2A and FIG. 2D vs. 2C). All T cell lines obtained expressed the CD4 phenotype as determined by flow cytometry (data not shown).

It is somewhat contradictory that $MBP_{93-105}$ specific T cells derived from MS patients produce less Th1 cytokines than those from healthy controls. One possibility is that although patients studied here did not receive any treatment 3 months prior to the study, some T cell lines were derived from patients that had previous treatment with beta-interferon (more than 5-9 months prior to the study) and their cytokine profile may be altered as a result. Beta-interferon has been shown to have a regulatory effect on the cytokine profile of T cells and the effect may be sustained after the termination of the treatment.

Example 3

Reactivity Pattern and TCR V Gene Usage of Cross-Reactive T Cell Clones

Figure 3:
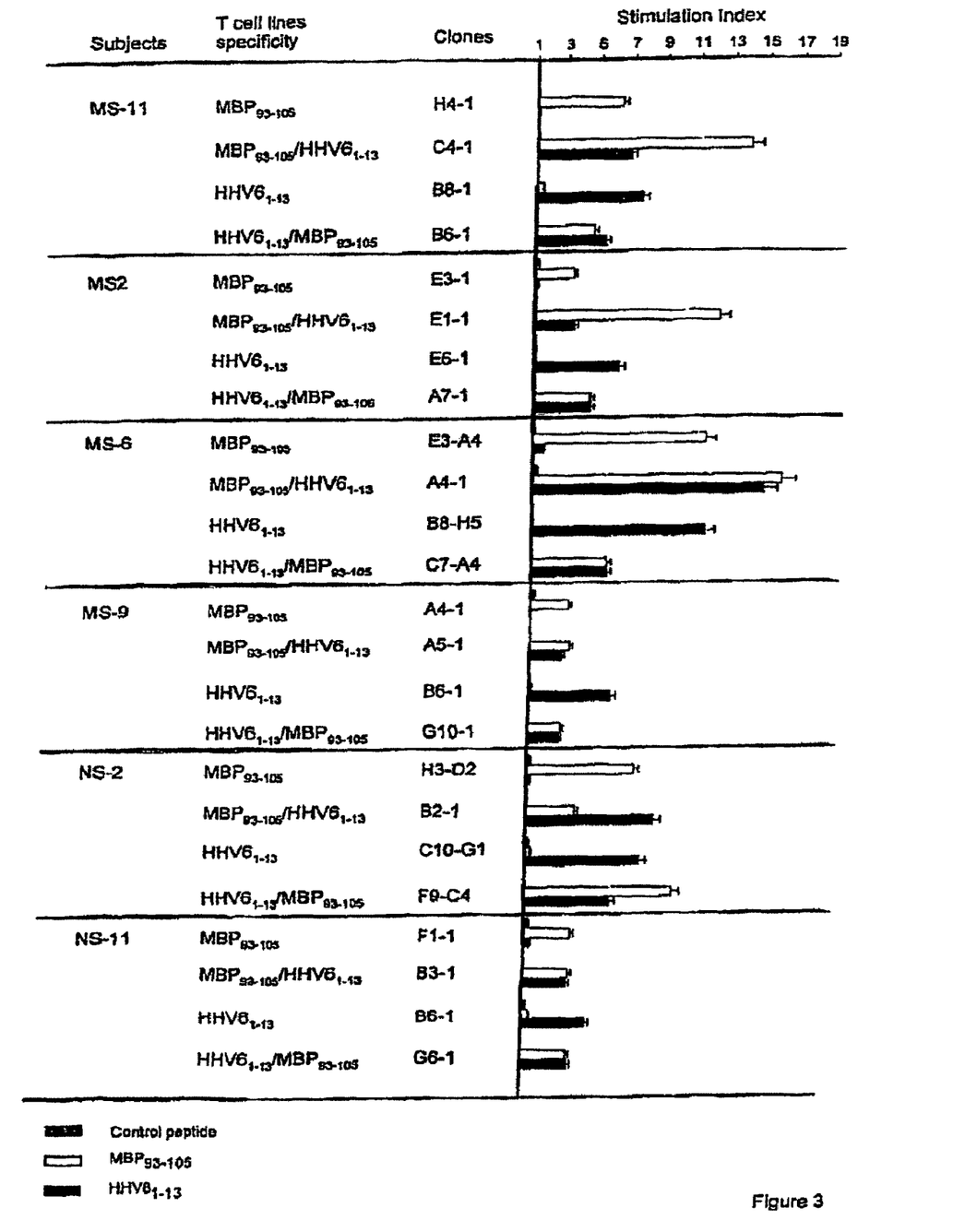
FIG. 3 shows the reactivity pattern of mono-specific and cross-reactive T cell clones to the MBP$_{93-105}$ and HHV-6 (U24)$_{1-13}$ peptides, or a control peptide (T cell receptor amino acid sequence: ASSENRASYNEQFFG) (SEQ ID NO: 7).

To confirm that the observed reactivity of the T cells recognizing both peptides of HHV-6 $(U24)_{1-13}$ and $MBP_{93-105}$ results from monoclonal T cell populations, cross-reactive T cell lines and mono-specific T cells lines described in Example 2 were characterized for their reactivity pattern to the individual peptides. As shown in FIG. 3, the T cell clones could be categorized, according to their reactivity to the peptides, into mono-specific T cell clones and cross-reactive T cell clones. The reactivity of the T cell clones was consistent with that of the parental T cell lines from which the T cell clones were generated.

The T cell clones were subsequently expanded in culture in an attempt to analyze the TCR V gene usage and CDR3 sequence. Unfortunately, the majority of the clones (18/24 clones) were lost during the process of expansion due to prolonged equipment/electric power failure and closing of the facility as a result of severe flood in the Houston area during the course of the study and only six clones survived.

Total cellular RNA was extracted from the six remaining independent T cell clones using RNeasy mini kit (QIAGEN, CA). TCR β chains were amplified by PCR with a set of Vβ-specific primers as by Wucherpfennig et al., "Shared human T cell receptor Vβ usage to immunodominant regions of myelin basic protein," Science 248:1016-1019 (1990) and Zang et al., "Restricted TCR Vα gene rearrangements in T cells recognizing an immunodominant peptide of myelin basic protein in DR2 patients with multiple sclerosis," Intern Immunol 10:991-998 (1998), which are hereby incorporated by reference in their entirety. Briefly, RNA was reverse transcribed to first-strand cDNA using an Oligo-dT primer and the superscript pre-amplification system (Gibco, MD). cDNA was amplified in a standard PCR using a set of primers specific for 24 Vβ gene families in combination with Cβ primer, respectively. For each PCR experiment, Cβ gene was amplified simultaneously to control the integrity of TCR cDNA. The amplification profile used was 1 min at 95° C. for denaturation, 20 sec at 56° C. for annealing, 40 sec at 72° C. for extension in a total of 35 cycles. The amplified PCR products were separated on a 1% agarose gel by electrophoresis and stained with ethidium bromide. The purified PCR products were directly sequenced with the T7 sequencing kit (Pharmacia, Uppsala, Sweden)[44].

As shown in Table 2, the six clones (including five cross-reactive T cell clones) examined were found to express single TCR BV genes and V-D-J junctional sequences, confirming monoclonality of the T cell clones.

Example 4

Serum Antibody Titers and the Reactivity Pattern to HHV-6 and MBP Peptides

We further addressed whether the increased T cell responses to both peptides of HHV-6 $(U24)_{1-13}$ and $MBP_{93-105}$ were consistent with potential B cell sensitization to the peptides in MS patients as compared to healthy controls. To this end, serum specimens freshly obtained from the same MS patients and the control subjects were examined for specific antibody reactivity to the peptides by ELISA.

Antibody titers were determined in serum specimens by ELISA. Briefly, microtiter plates were coated overnight at 4° C. with the peptides at 5 µg/ml in a carbonate buffer (100 mM, pH 9.5). An irrelevant peptide and $MBP_{41-59}$ were used as reference peptides. Non-specific binding sites were saturated with FBS-PBS for 1 hour and washed subsequently with PBS-T. Serum samples were prepared in serial dilutions (1:50, 1:100, 1:500) with FBS-PBS and 100 µl of each sample were added in duplicate wells. The rest of the procedure is the same as that described above.

Figure 4:
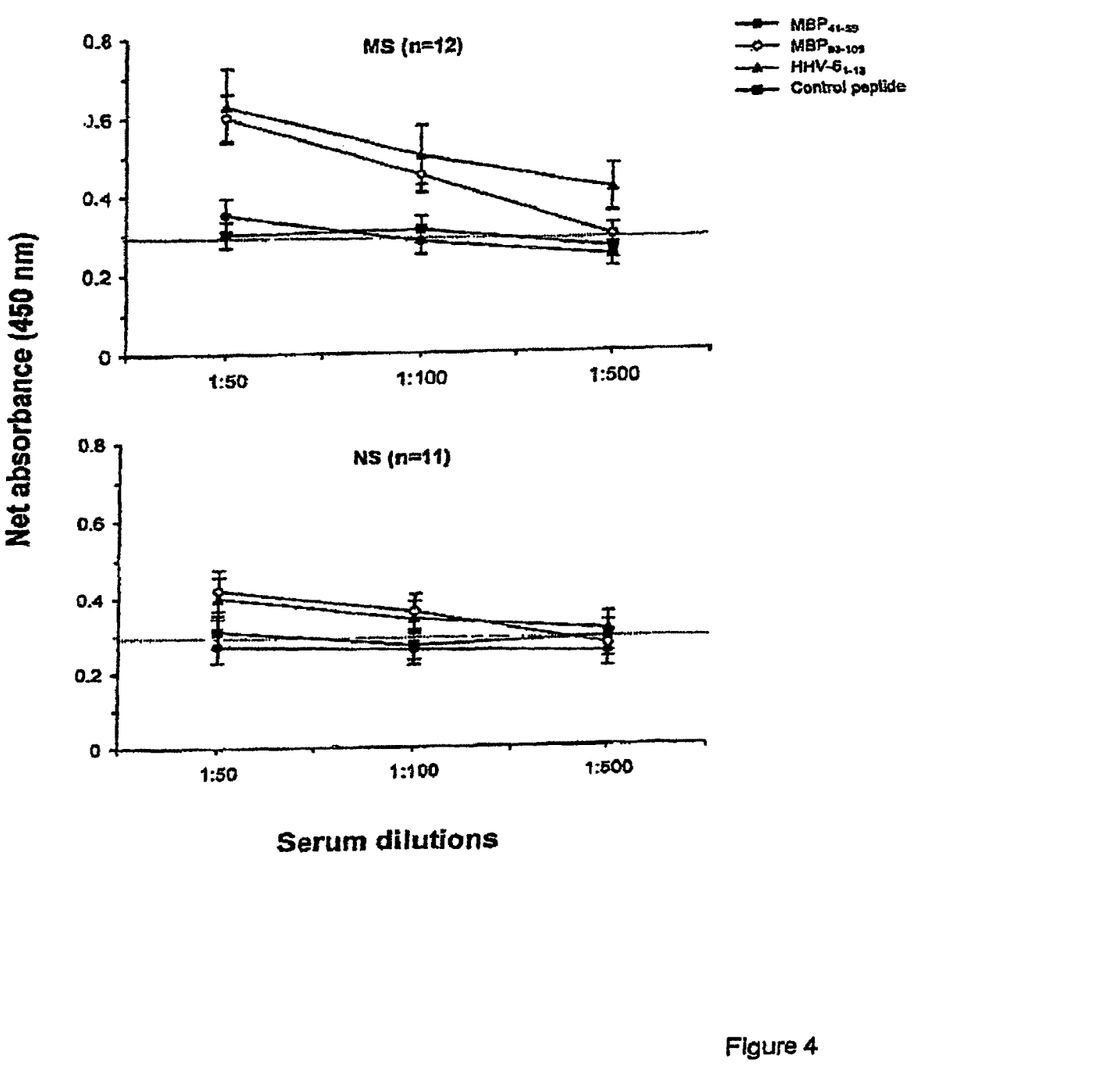
FIG. 4 shows serum IgG antibodies specific for the MBP$_{93-105}$ and HHV-6$_{1-13}$ peptides in MS patients and healthy subjects compared to a control peptide (T cell receptor amino acid sequence: ASSENRASYNEQFFG) (SEQ ID NO: 7).

As illustrated in FIG. 4, the results showed that the antibody titers for both peptide HHV-6 $(U24)_{1-13}$ and peptide $MBP_{93-105}$ were elevated at the serum dilutions of 1:50 and 1:100 in MS patients as compared to those detected in control subjects.

Example 5

Vaccination of MS Patient Using Autologous Cross-Reactive T Cells

The observation in Example 1 that the precursor frequency of cross-reactive T cells is significantly elevated in MS patients suggests that these T cells are sensitized in vivo in patients with MS. The possibility that the immune system is sensitized to the peptides in MS patients is further strengthened by the increase in antibody titers for both peptides in serum specimens obtained from the MS cohort. The findings are consistent with a number of recent reports indicating the increased replication of HHV-6 in MS patients as evident by more frequent detection of elevated cell-free viral DNA of HHV-6 in serum and cerebrospinal fluid specimens obtained from MS patients. It is likely that active replication of HHV-6 may be responsible for the observed sensitization of the immune system to the 93-105 region of MBP in MS as peptide $MBP_{93-105}$ shares an identical sequence with peptide HHV-6 $(U24)_{1-13}$.

Although the T cell recognition of MBP in MS patients is relatively heterogeneous, some regions of MBP have immunodominant properties, such as the 84-102/83-99 region and the 151-170 region of MBP. The immunodominant properties of these regions may be associated with their binding affinity to HLA-DR (DRB 1*1501) preferentially expressed in the MS population. It has been demonstrated that peptides corresponding to both the 84-103 and the 144-163 regions have the highest binding affinity to DRB1*1501. Although the 93-105 region of MBP homologues and the 1-13 region of HHV-6 (U24) have an overlap of 4 amino acids (PRTP) (SEQ ID NO:11) with the 83-99 immunodominant region of MBP, the PRTP sequence alone is not sufficient to form an individual T cell epitope and is unlikely to represent the immunodominant T cell epitopes. Indeed, additional experiments revealed no cross-reactivity between the T cell responses to the $MBP_{83-99}$ peptide and the $MBP_{93-105}$ peptide when four independent $MBP_{83-99}$ specific T cell clones and six $MBP_{93-105}$ specific T cell clones were examined (data not shown).

83-99 peptide of MBP, which demonstrated that the different role of the central versus flanking residues, allowing some degree of promiscuity in T cell recognition. The results described herein provide new evidence indicating the association between HHV-6 and autoreactive immune responses to MBP, which has particular importance and clinical relevance because of the potential involvement of the two agents, as a candidate myelin autoantigen and a suspected etiologic agent, in the pathogenesis of MS. The results herein indicate that MS may be prevented or treated in patients infected with HHV-6 by administering antiviral agents which eliminate or reduce reactivation of latent HHV-6 and optionally inactivated autoreactive or cross-reactive T cells or peptides corresponding to the V-D-J region of autoreactive or cross-reactive T cells, or a combination thereof.

TABLE 1

Clinical characteristics and demographic information, serum cell-free HHV-6 DNA and HLA types of MS patients and control subjects

| Subjects | Age | Sex | Type of MS | Disease Duration (yrs.) | EDSS | Serum cell-free HHV-6 DNA | HLA-DR genotypes |
| --- | --- | --- | --- | --- | --- | --- | --- |
| MS-1 | 44 | M | RR | 5 | 3.0 | − | B1*1501; B1*1301; B3*0101; B5*0101 |
| MS-2 | 38 | F | RR | 2 | 1.0 | + | B1*0405; B1*1301; B3*0101; B4*0103 |
| MS-3 | 46 | F | RR | 4 | 3.0 | + | B1*1501; B1*0405; B5*0101; B4*0103 |
| MS-4 | 47 | F | SP | 7 | 7.0 | + | B1*1501; B1*1502; B5*0101; B5*0102 |
| MS-5 | 45 | F | RR | 4 | 1.5 | + | B1*5101; B1*0404; B5*0101; B4*0131 |
| MS-6 | 60 | F | SP | 11 | 6.6 | − | B1*1301; B1*0802; B3*0101 |
| MS-7 | 51 | F | SP | 13 | 3.5 | + | B1*0103; B1*0802 |
| MS-8 | 57 | F | RR | 6 | 1.5 | + | B1*1501; B1*0404; B5*0101; B4*0131 |
| MS-9 | 46 | F | RR | 6 | 1.5 | + | B1*1501; B1*1104; B3*0202; B5*0101 |
| MS-10 | 41 | F | SP | 13 | 6.0 | + | B1*1602; B1*0408; B5*0202; B4*0103 |
| MS-11 | 31 | F | RR | 4 | 1.0 | + | B1*1602; B1*1303; B3*0101; B5*0202 |
| MS-12 | 50 | F | SP | 28 | 7.0 | + | B1*1101; B1*0701; B3*0202; B4*0101 |
| NS-1 | 47 | M | — | — | — | − | B1*1501; B1*0701; B5*0101; B4*0103 |
| NS-2 | 49 | F | — | — | — | − | B1*0102; B1*0405; B4*0131 |
| NS-3 | 35 | M | — | — | — | − | B1*1503; B1*1301; B3*0101 |
| NS-4 | 32 | F | — | — | — | + | B1*0103; B1*1402; B3*0101 |
| NS-5 | 46 | F | — | — | — | + | B1*1101; B1*0701; B3*0202; B4*0101 |
| NS-6 | 60 | F | — | — | — | + | B1*1501; B1*0404; B5*0101; B4*0131 |
| NS-7 | 33 | F | — | — | — | − | B1*0103; B1*1104; B3*0202 |
| NS-8 | 34 | F | — | — | — | + | B1*1503; B1*1301; B3*0101; B5*0101 |
| NS-9 | 43 | F | — | — | — | + | B1*0101; B1*0405; B4*0131 |
| NS-10 | 46 | F | — | — | — | − | B1*0301; B1*0802; B3*0101 |
| NS-11 | 30 | F | — | — | — | + | B1*1501; B1*1402; B3*0101 |

RR, relapsing-remitting MS;
SP, secondary progressive MS.
EDSS, expanded disability scales score.
Cell-free viral DNA for HHV-6 was detected in serum specimens derived from the subjects using nested PCR and Southern hybridization with specific primers and probes[33].
The results are expressed as detectable (+) (>5 DNA copies/μl) and undetectable (−).

However, the possibility exists that the increased T cell sensitization to MBP in MS patients may be initially triggered by the HHV-6 antigen that shares the sequence homology with $MBP_{93-105}$ and later spreads to other epitopes of MBP by the mechanism known as epitope spreading. As the immunodominant properties of the T cell epitopes are preferentially associated with the HLA-DR molecules expressed in MS patients regardless of the sequence of stimulation events, the triggering epitope(s) of MBP, such as $MBP_{93-105}$ that does not have high binding affinity, may not manifest itself as an immunodominant epitope when the disease is established.

The findings suggest that the cross-reactive T cells recognizing both MBP and HHV-6 peptides represent a significant subset of T cells with some degree of TCR degeneracy. It appears that the recognition of the cross-reactive T cells has a less stringent requirement for the flanking residues of the two peptides. In contrast, these flanking residues are critical for the T cell recognition of mono-specific T cells. Similar findings have also been described for the T cell recognition of the

TABLE 2

TCR VDJ region sequence of the cross-reactive T cell clones

| SEQ ID NO: | Clone | BV | V-D-J | BC |
| --- | --- | --- | --- | --- |
| 1 | MS11C4-1 | BV5 | YLCASSLVRDSGYTFGSGTRLTVV | EDLNK |
| 2 | MS11B6-1 | BV22 | YFCASSENRASYNEQFFGPGTPLTVL | EDLKN |
| 3 | MS2E1-1 | BV13 | YFCASSLGRLINSPLHFGNGTRLTVT | EDLNK |
| 4 | MS2A7-1 | BV12 | YFCAISEDGNYGYTFGSGTRLTVV | EDLNK |
| 5 | MS2-E3-1 | BV8 | YFCASSLRAGGYQYGYTFGSGTRLTVV | EDLNK |
| 6 | MS9-A5-1 | BV2 | FYICSASLGMGDIQYFGAGTRLSVL | EDLKN |

What is claimed is:

1. A method for isolating one or more T cells that cross-react with a self-antigen and a foreign antigen comprising:
   (a) incubating a sample comprising T cells with a foreign antigen consisting of residues 1-13 of human herpesvirus-6 U24 (SEQ ID NO:9), wherein said sample optionally comprises one or more autoantigens; and
   b) isolating the one or more cross-reactive T cells by cloning or direct expansion.

2. The method of claim 1, wherein the autoantigen is selected from the group consisting of myelin basic protein, proteolipid protein, myelin oligodendrocyte glycoprotein, collagen type II peptides, heat shock protein, MAGE, PSA, CA125, GAD protein, and tumor associated antigen.

3. The method of claim 1, wherein the autoantigen comprises an immunodominant epitope of a member selected from the group consisting of myelin basic protein, proteolipid protein, myelin oligodendrocyte glycoprotein, collagen type II peptides, heat shock protein, MAGE, PSA, CA125, GAD protein, and tumor associates antigen.

4. The method of claim 1, further comprising selecting one or more T cells that express one or more first markers selected from the group consisting of CD69, CD4, CD25, CD36 and HLADR and one or more second markers selected from the group consisting of IL-2, IFNγ, TNFα, IL5, IL-10 and IL-13.

5. The method of claim 4, wherein the autoantigen is selected from the group consisting of myelin basic protein, proteolipid protein, myelin oligodendrocyte glycoprotein, collagen type II peptides, heat shock protein, MAGE, PSA, CA125, GAD protein, and tumor associated antigen.

6. The method of claim 4, wherein the cells expressing said first and said second markers are selected using antibodies to said first and second markers respectively, or optionally a bi-specific antibody which binds both first and second markers in combination with an antibody which binds said second marker.

7. The method of claim 6, wherein one or more of said antibodies is fluorescently labeled and wherein said T cell is selected by fluorescent activated cell sorting.

8. The method of claim 6, wherein said first antibody is conjugated to a magnetic microbead and wherein said T cell is selected by magnetic activated cell sorting.

9. A method for producing a composition comprising one or more T cells that cross-react with a self antigen and a foreign antigen, comprising:
   (a) incubating a sample derived from a patient comprising T cells with a foreign antigen consisting of residues 1-13 of human herpesvirus-6 U24 (SEQ ID NO:9), wherein said sample optionally comprises one or more autoantigens;
   (b) selecting one or more T cells that express one or more first markers selected from the group consisting of CD69, CD4, CD25, CD36 and HLADR and one or more second markers selected from the group consisting of IL-2, IFNγ, TNFα, IL5, IL-10 and IL-13; and
   (c) inactivating the T cells selected by step (b).

10. The method of claim 9 further comprising expanding the number of T cells selected in step (b).

* * * * *